United States Patent
Lash et al.

(10) Patent No.: US 7,538,865 B2
(45) Date of Patent: *May 26, 2009

(54) SOURCE AND DETECTOR SENSOR ARRANGEMENT

(75) Inventors: Robert E Lash, Redwood City, CA (US); Jimmy Jian-min Mao, Fremont, CA (US); Qiong Lin, Fremont, CA (US)

(73) Assignee: ViOptix, Inc., Fremont, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/968,519

(22) Filed: Jan. 2, 2008

(65) Prior Publication Data

US 2008/0108886 A1 May 8, 2008

Related U.S. Application Data

(63) Continuation of application No. 11/162,376, filed on Sep. 8, 2005, now Pat. No. 7,355,688.

(51) Int. Cl.
*G01J 1/42* (2006.01)
(52) U.S. Cl. ............... 356/222; 356/213; 356/446; 600/310; 600/340
(58) Field of Classification Search ............ 356/221, 356/222, 213, 446
See application file for complete search history.

(56) References Cited

U.S. PATENT DOCUMENTS

| | | | |
|---|---|---|---|
| 5,088,493 | A | 2/1992 | Giannini et al. |
| 6,078,833 | A | 6/2000 | Hueber |
| 6,285,904 | B1 | 9/2001 | Weber et al. |
| 6,549,284 | B1 | 4/2003 | Boas et al. |
| 6,587,703 | B2 | 7/2003 | Cheng et al. |
| 6,597,931 | B1 | 7/2003 | Cheng et al. |
| 6,708,048 | B1 | 3/2004 | Chance |
| 7,254,427 | B2 | 8/2007 | Cho et al. |
| 2004/0111016 | A1 | 6/2004 | Casscells et al. |

OTHER PUBLICATIONS

Hueber, Dennis et al., "New Optical Probe Designs for Absolute (Self-Calibrating) NIR Tissue Hemoglobin Measurements," Proceedings of Optical Tomography and Spectroscopy of Tissue III, Jan. 1999, 618-631, vol. 3597.

*Primary Examiner*—L. G Lauchman
(74) *Attorney, Agent, or Firm*—Aka Chan LLP (57) ABSTRACT

A device has various arrangements of source and detector sensors. In specific implementations, the device has at least four structures, one source and three detectors, two sources and two detectors, and other arrangement variations. In a specific implementation, between a source structure and a detector structure, there are not any other intervening sensor structures. The device may be part of a medical device that is used to monitor or measure oxygen saturation levels in a tissue.

28 Claims, 7 Drawing Sheets

SOURCE AND DETECTOR SENSOR ARRANGEMENT

CROSS-REFERENCE TO RELATED APPLICATION

This patent application is a continuation of U.S. patent application Ser. No. 11/162,376, filed Sep. 8, 2005, which is incorporated by reference.

BACKGROUND OF THE INVENTION

The present invention relates generally to optical imaging systems that monitor oxygen levels in tissue. More specifically, the present invention relates to optical probes that include sources and detectors that are not symmetrically arranged on sensor heads of the optical probes.

Near-infrared spectroscopy has been used for noninvasive measurement of various physiological properties in animal and human subjects. The basic principle underlying the near-infrared spectroscopy is that physiological tissues include various highly-scattering chromophores to the near-infrared waves with relatively low absorption. Many substances in a medium may interact or interfere with the near-infrared light waves propagating therethrough. Human tissues, for example, include numerous chromophores such as oxygenated hemoglobin, deoxygenated hemoglobin, water, lipid, and cytochrome, where the hemoglobins are the dominant chromophores in the spectrum range of approximately 700 nanometers to approximately 900 nanometers. Accordingly, the near-infrared spectroscope has been applied to measure oxygen levels in the physiological medium such as tissue hemoglobin oxygen saturation and total hemoglobin concentrations.

Various techniques have been developed for the near-infrared spectroscopy, e.g., time-resolved spectroscopy (TRS), phase modulation spectroscopy (PMS), and continuous wave spectroscopy (CWS). In a homogeneous and semi-infinite model, both TRS and PMS have been used to obtain spectra of an absorption coefficient and reduced scattering coefficient of the physiological medium by solving a photon diffusion equation, and to calculate concentrations of oxygenated and deoxygenated hemoglobins as well as tissue oxygen saturation. CWS has generally been designed to solve a modified Beer-Lambert equation and to measure changes in the concentrations of oxygenated and deoxygenated hemoglobins.

Despite their capability of providing the hemoglobin concentrations as well as the oxygen saturation, one major drawback of TRS and PMS is that the equipment is bulky and expensive. CWS may be manufactured at a lower cost but is limited in its utility because it cannot compute the oxygen saturation from the changes in the concentrations of oxygenated and deoxygenated hemoglobins.

Optical diffusion imaging and spectroscopy (ODIS) allows tissue to be characterized based on measurements of photon scattering and absorption. In tissue such as human tissue, near-infrared light is highly scattered and minimally absorbed. Optical diffusion imaging is achieved by sending optical signals into tissue and measuring the corresponding diffuse reflectance or transmittance on the tissue surface.

Scattering is caused by the heterogeneous structure of a tissue and, therefore, is an indicator of the density of a cell and the nuclear size of the cell. Absorption is caused by interaction with chromophores. ODIS emits light into tissue through a sensor. The position of the light source which emits the light and a detector which detects the light allows a depth of measurement to be determined. A ratio of oxyhemoglobin and deoxyhemoglobin may be used to allow for substantially real-time measurement of oxygen, e.g., oxygen saturation levels.

Within ODIS systems, sensors which come into contact with tissue surfaces generally have optical fibers arranged thereon in a substantially symmetric layout. That is, optical fibers that are coupled to light sources are arranged in a substantially symmetric orientation relative to optical fibers that are coupled to light detectors. While a symmetric orientation is effective in allowing for oxygen saturation levels to be measured, the manufacture of such sensor is often difficult, as the exact placement of the optical fibers within the sensor is crucial. Further, when the anatomy of tissue or underlying structure is not substantially symmetric, the use of a sensor with a symmetric orientation may not allow for accurate measurements to be readily made.

Therefore, what is needed is a sensor that is relatively easy to manufacture, and is arranged to be used on tissue which may not have a symmetric anatomy. That is, what is desired is a sensor with a layout of optical fibers for light sources and optical fibers for detectors that facilitates use with tissue having substantially any anatomy.

BRIEF SUMMARY OF THE INVENTION

A device has various arrangements of source and detector sensors. In specific implementations, the device has at least four structures, one source and three detectors, two sources and two detectors, and other arrangements. In a specific implementation, between a source structure and a detector structure, there are not any other intervening sensor structures. The device may be part of a medical device that is used to monitor or measure, or both, oxygen saturation levels in a tissue.

In a specific implementation, the device is used in the implementation of a medical device probe. When used, such a probe is placed against or near tissue to be measured, radiation is emitted from one or more of the sources, reflected or transmitted through the tissue, and received by one or more of the detectors. Multiple different wavelengths of radiation may be emitted. The amount of the attenuation between the signal radiated and signal detected is used in determining oxygen saturation levels.

The present invention relates to a probe with a sensor that supports source fibers and detector fibers such that the source fibers have a substantially nonsymmetric arrangement relative to the detector fibers. According to one aspect of the present invention, a sensor arrangement that is suitable for use in an optical imaging system and is arranged to contact a body such as tissue includes a first source structure, a second source structure, and a detector arrangement. The first source structure provides a first beam of light and the second source structure provides a second beam of light.

The detector arrangement includes detector structures and receives the first beam of light and the second beam of light after the first beam of light and the second beam of light are reflected off of the body. The detector arrangement is arranged to define a first axis, and a distance from the first source structure to the first axis is not equal to a distance from the second source structure to the first axis.

In one embodiment, a difference between the distance from the first source structure to the first axis and the distance from the second source structure is at least approximately 0.03 millimeters. In such an embodiment, the distance from the first source structure to the first axis may be approximately 0.020 millimeters and the distance from the second source structure to the first axis may be approximately 0.24 millimeters.

In an embodiment, a probe with a sensor or a sensor head that has source structures in a nonsymmetric orientation with respect to detector structures enables the sensor head to be utilized to monitor tissue with an underlying anatomy that is not substantially symmetric. The lack of symmetry also effectively loosens manufacturing tolerances associated with the manufacture of such sensor. Any attenuation associated with the offset orientation of optical fibers that are coupled to light sources is typically compensated for through the use of software executing with respect to an optical imaging system. Hence, the amount of compensation applied may be relatively easily varied as needed to accommodate inaccuracies in the positioning of optical fibers with respect to the sensor.

According to another aspect of the present invention, a sensor arrangement that is suitable for use in an optical imaging system includes a first source structure that is arranged to provide a first beam of light and a second source structure that is arranged to provide a second beam of light. The sensor arrangement also includes a detector arrangement that has a first detector structure and a second detector structure. The detector arrangement is arranged to receive the first beam of light and the second beam of light after the first beam of light and the second beam of light are reflected off of or transmitted through tissue. An orientation of the first source structure with respect to the detector arrangement is not symmetric relative to an orientation of the second source structure with respect to the detector arrangement.

According to yet another aspect of the present invention, a method for taking an oxygen saturation measurement of tissue using an optical system that utilizes a probe with a sensor head in which a first source structure and a second source structure are offset relative to detector structures involves positioning the sensor head in contact with the tissue and transmitting light into the tissue through the first source structure and the second source structure. The method also involves receiving reflected light from the tissue at the detector structures that includes attenuation characteristics, and processing the reflected light using a number of photodetectors. Processing the reflected light using the number of photodetectors includes compensating for the attenuation characteristics using an attenuation compensator.

In accordance with still another aspect of the present invention, a probe which may be used as a part of an optical system to monitor oxygen levels in tissue includes a coupling interface that allows the probe to be coupled to light sources and detectors. A sensor head of the probe is arranged to contact the tissue, and supports a first source structure, a second source structure, and a detector arrangement. The first source structure and the second source structure are coupled to the light sources via the coupling interface, while the detector arrangement is coupled to the detectors through the coupling interface. An orientation of the first source structure relative to the detector arrangement is not symmetric with respect to an orientation of the second source structure relative to the detector arrangement.

In one embodiment, the detector arrangement includes detector structures. In such an embodiment, the detector arrangement receives the first beam of light and the second beam of light after the first beam of light and the second beam of light are reflected off of or transmitted through the tissue. The detector arrangement defines a first axis that passes through each detector structure of the detector structures such that a distance from the first source structure to the first axis is unequal to a distance from the second source structure to the first axis.

In an embodiment, the invention is a device including: a first source structure; a first detector structure; a second detector structure; and a third detector structure, where the second detector structure is between the first and third detector structures. The first source structure, first detector structure, and third detector structure form vertices of a first right triangle. A hypotenuse of the first right triangle extends from the first source structure to the third detector structure without touching another source or detector structure.

In an embodiment, the invention is a device including: a first source, a first detector, a second detector, and a third detector, where the second detector is between the first and third detectors. The first source, first detector, and third detector form vertices of a triangle having an obtuse angle. A longest side of the triangle extends from the first source to the third detector without touching another source or detector.

In an embodiment, the invention is a device including: a first source, a second source, a first detector, and a second detector. The first detector includes optical fiber. A first distance extends between the first source and the first detector without touching another source or detector. A second distance extends between the second source and the second detector without touching another source or detector. The first distance is different from the second distance.

Other objects, features, and advantages of the present invention will become apparent upon consideration of the following detailed description and the accompanying drawings, in which like reference designations represent like features throughout the figures.

DETAILED DESCRIPTION OF THE INVENTION

A sensor head which is such that optical fibers that are coupled to light sources are arranged in an offset orientation relative to optical fibers that are coupled to detectors allows the sensor head to be utilized in areas in which tissue being monitored is not substantially symmetric. Any attenuation associated with the offset orientation of optical fibers that are coupled to light sources is typically compensated for through software. Such a sensor head is relatively easy to manufacture in that the placement of optical fibers that are coupled to light sources is less rigid, i.e., any slight variation in the placement of the optical fibers may be corrected for using the software that compensates for attenuation. In addition, the use of software to compensate for attenuation associated with the placement of optical fibers on a sensor head essentially enables the sensor head to be used with both symmetric and asymmetric tissue anatomies.

As will be understood by those skilled in the art, a volume of tissue substantially immediately beneath a sensor head may either be homogeneous or inhomogeneous depending upon the actual anatomical structures contained within this volume. By way of example, when a sensor head is positioned on skin overlying a thick region of adipose tissue, the distribution of signet cells and capillaries containing oxygenated hemoglobin is generally relatively uniform, i.e., symmetric and homogenous. However, a sensor head may be positioned over a tissue volume in which underlying structure include arteries, veins, bone, tendon, cartilage, fascia, muscle, or pigmented lesions. Such tissue may have asymmetric anatomies that cause light to be reflected or absorbed asymmetrically due, for example, to regions that are either unusually reflective or absorptive. Software that compensates for attenuation may eliminate readings associated with light that reflects off of structures such as bone. Optical fibers that are coupled to sources and are positioned in a sensor head in an offset orientation relative to optical fibers coupled to detectors may facilitate the transmission and reading of light that avoids structures such as bone. Hence, the use of offset source optical fiber orientations facilitate the creation of specialized sensor heads that may be used to measure oxygen saturation in many different parts of a body.

Figure 1A:
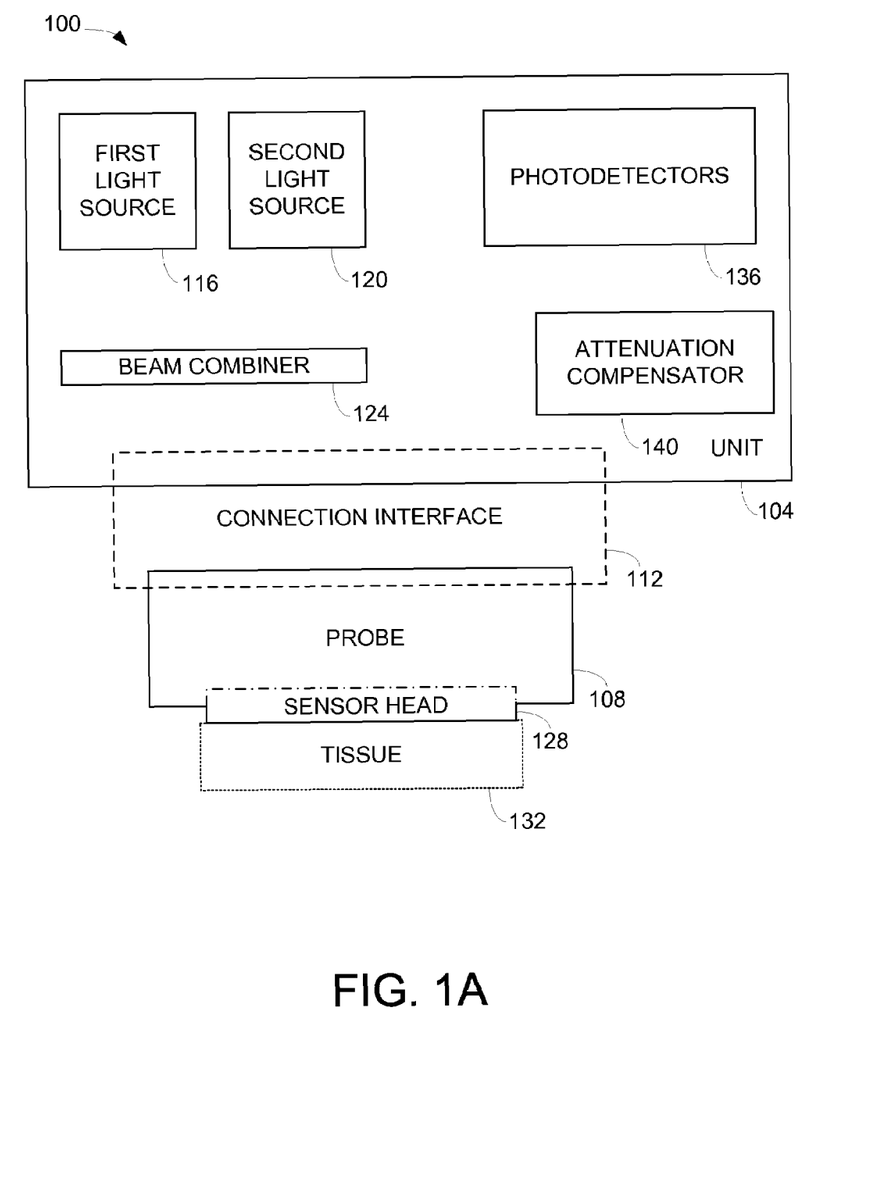
FIG. 1A shows a block diagram representation of an optical imaging system with a sensor head which includes sources in an offset arrangement relative to detectors in accordance with an embodiment of the present invention.

FIG. 1A shows a block diagram representation of an optical imaging system with a sensor head that includes source arrangements arranged in an offset orientation relative to detector arrangements in accordance with an embodiment of the present invention. An optical imaging system 100 includes a unit 104 and a probe 108 that are coupled via a connection interface 112. Connection interface 112 is generally a light-tight interconnection with a laser safety interlock that is arranged to substantially prevent laser light from being emitted through connection interface 112 when probe 108 is not coupled to unit 104. Connection interface 112 typically includes a panel connector (not shown) attached to unit 104 and a cable connector (not shown) attached to probe 108.

Unit 104 includes a first light source 116 and a second light source 120. First light source 116 and second light source 120, in the described embodiment, are each dual wavelength light sources. In other words, first light source 116 provides two wavelengths of light and second light source 120 provides two wavelengths of light. First light source 116 and second light source 120 may each include a laser diode that provides a light beam or pulse at a lower frequency and a laser diode that provides a light beam or pulse at a higher frequency. By way of example, first light source 116 and second light source 120 may each include a laser diode that produces visible red light of an approximately 690-nanometer wavelength and a laser diode that produces near-infrared light of an approximately 830-nanometer wavelength. It should be appreciated, however, that the wavelengths of light produced by laser diodes associated with first light source 116 and second light source 120 may vary widely.

Light emitted by first light source 116 and light emitted by second light source 120 is provided to a beam combiner 124 via optical fibers (not shown). Each laser diode associated with first light source 116 and each laser diode associated with second light source 120 is provided on a separate optical fiber (not shown). Beam combiner 124 effectively merges the light from the laser diodes of first light source 116 and merges the light from the laser diodes of second light source 120. The merged light is then provided via output fibers (not shown) to connection interface 112. The output fibers are arranged to allow the merged or combined light to be homogenized to ensure that the light is substantially uniformly distributed across the output fibers when the light enters connection interface 112.

Through connection interface 112, light is provided to a sensor head 128 of probe 108. Within sensor head 128, optical fibers (not shown) provide the merged light associated with first light source 116 and the merged light associated with second light source 120 to a surface of sensor head 128 that is arranged to come into contact with tissue 132. The optical fibers (not shown) are positioned such that they have an offset orientation with respect to optical fibers (not shown) that are associated with photodetectors 136 within unit 104. The orientation of source optical fibers and detector optical fibers will be described below with respect to FIGS. 2A-2C.

When sensor head 128 causes light to be transmitted into tissue 132, the reflected light is collected by optical detector fibers (not shown) that are coupled to photodetectors 136. In general, at least two photodetectors 136 are included within unit 104 and are configured to be sensitive to the light which is transmitted by first light source 116 and second light source 120. An attenuation compensator 140 within unit 104 is generally arranged to compensate for any attenuation in the reflected light that results from the offset orientation of source optical fibers (not shown) relative to detector optical fibers (not shown). In one embodiment, attenuation compensator 140 effectively provides compensation using a mathematical algorithm that constructs ratios in which attenuation coefficients may be found in both a numerator and a denominator and hence, may be canceled out. Such ratios may use light intensities as detected by photodetectors 136 in such a way that attenuation factors have little effect on the evaluation of optical properties of tissue 132 beneath sensor head 128. It should be appreciated that attenuation compensator 140 may generally be substantially incorporated into software or firmware that executes an algorithm that determines oxygen saturation levels.

Figure 1B:
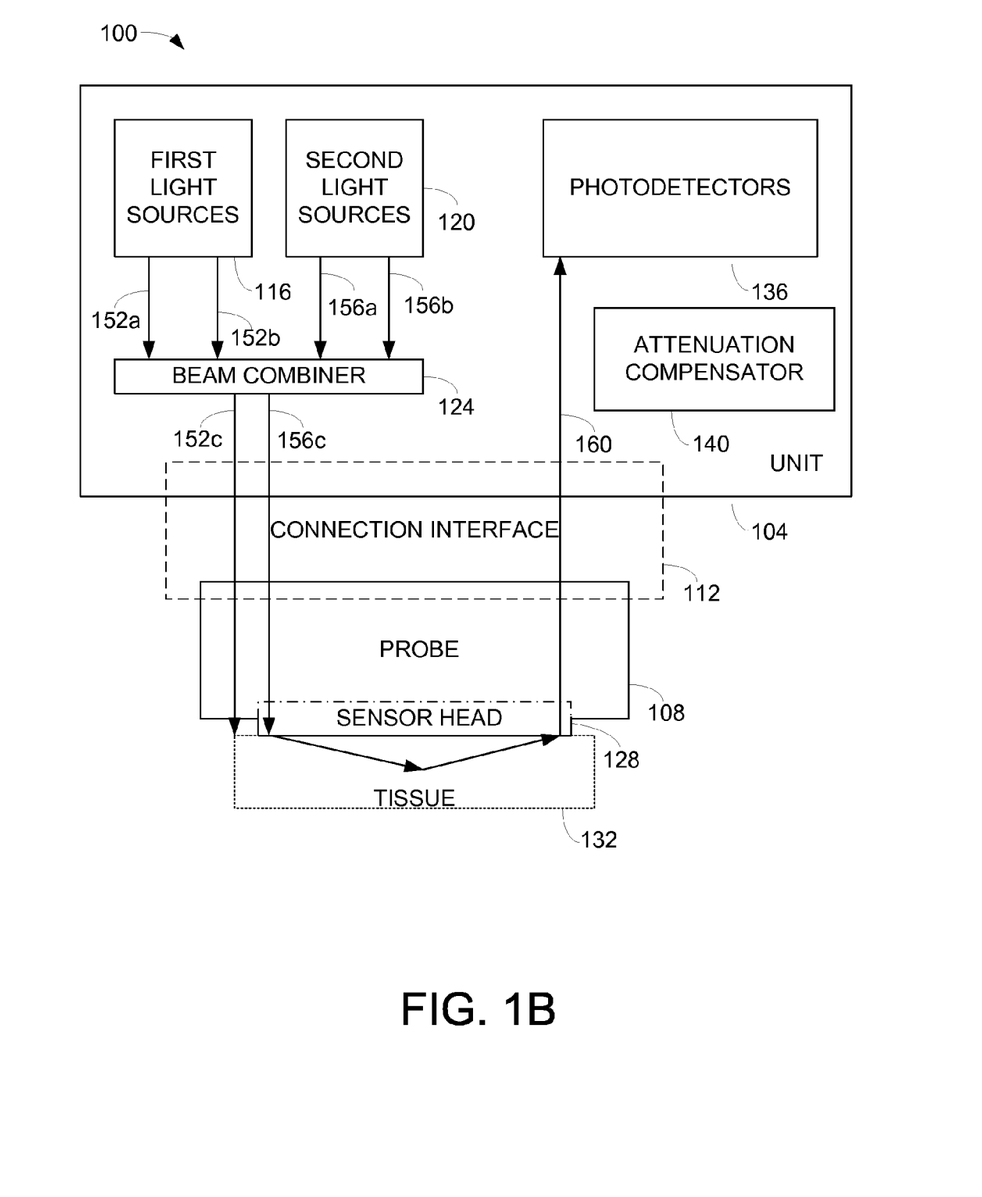
FIG. 1B shows a block diagram representation of an optical imaging system with a sensor head which includes sources in an offset arrangement relative to detectors, i.e., optical imaging system 100 of FIG. 1A, in accordance with an embodiment of the present invention.

FIG. 1B shows a block diagram representation of optical imaging system 100 of FIG. 1A which shows the path of light emitted by light sources, i.e., first light source 116 and second light source 120 of FIG. 1A, in accordance with an embodiment of the present invention. When first light source 116 emits light at two wavelengths, light of the first wavelength 152a and light of the second wavelength 152b are provided to beam combiner 124 which effectively merges the light into a light stream 152c that is provided to sensor head 128, e.g., through optical source fibers. Similarly, when second light source 120 emits light at two wavelengths, light of the first wavelength 156a and light of the second wavelength 156b are merged into a light stream 156c by beam combiner 124 that is provided to sensor head 128. Light streams 152c, 156c are transmitted into tissue 132 reflect off of tissue 132, through sensor head 128 to photodetectors 136.

Figure 2A:
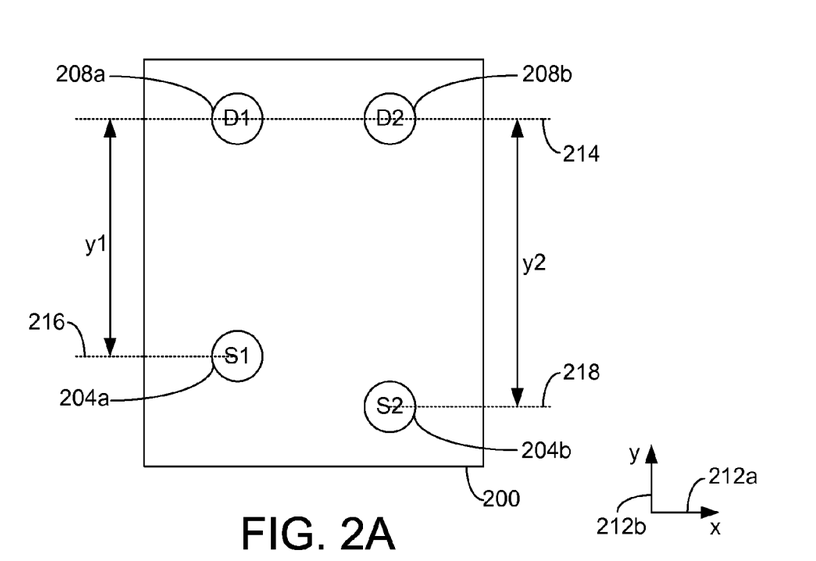
FIG. 2A shows a sensor head with a pair of light sources that are in an offset arrangement relative to a pair of detectors in accordance with an embodiment of the present invention.

As previously mentioned, optical source fibers are arranged such that at a surface of a sensor head that is arranged to come into contact with tissue, the optical source fibers have an offset orientation relative to optical detector fibers. With reference to FIG. 2A, the orientation of source fibers with respect to detector fibers will be described in accordance with an embodiment of the present invention. A sensor head 200, which may be of substantially any shape or size, is a part of a probe that is a part of an overall system that measures oxygen saturation levels in tissue. Sensor head 200 is arranged to accommodate source arrangements 204a, 204b, and detector arrangements 208a, 208b. For ease of discussion, although source arrangements 204a, 204b are generally fiber optic cables or optical fibers coupled to light sources and detector arrangements 208a, 208b are generally fiber optic cables or optical fibers coupled to photodetectors, source arrangements 204a, 204b are referred to in this application as sources and detector arrangements 208a, 208b are referred to in this application as detectors.

Sources 204a, 204b are arranged such that they are in an offset arrangement relative to detectors 208a, 208b. That is, source 204a and source 204b are not equidistant to detectors 208a, 208b relative to at least one axis. Detectors 208a, 208b are arranged such that a centerline 214 of detectors 208a, 208b is approximately parallel to an x-axis 212a. Typically, centerline 214 passes through a centerpoint of each detector 208a, 208b. Sources 204a, 204b are arranged such that a centerline 216 of source 204a is parallel to a centerline 218 of source 204b, but is not coincident with centerline 218. Centerline 216 passes through a centerpoint of source 204a and is parallel to x-axis 212a, while centerline 218 passes through a centerpoint of source 204b and is parallel to x-axis 212a.

A distance y1 between centerline 214 and centerline 216 along a y-axis 212b differs from a distance y2 between centerline 214 and centerline 218. Although distance y2 is shown as being greater than distance y1, it should be appreciated that distance y1 may instead be greater than y2. The difference between distance y2 and distance y1 is generally characteristic of the offset arrangement, or substantially unbalanced arrangement, of sources 204a, 204b relative to detectors 208a, 208b. In other words, there is effectively a lack of symmetry in the placement of sources 204a, 204b.

Figure 2B:
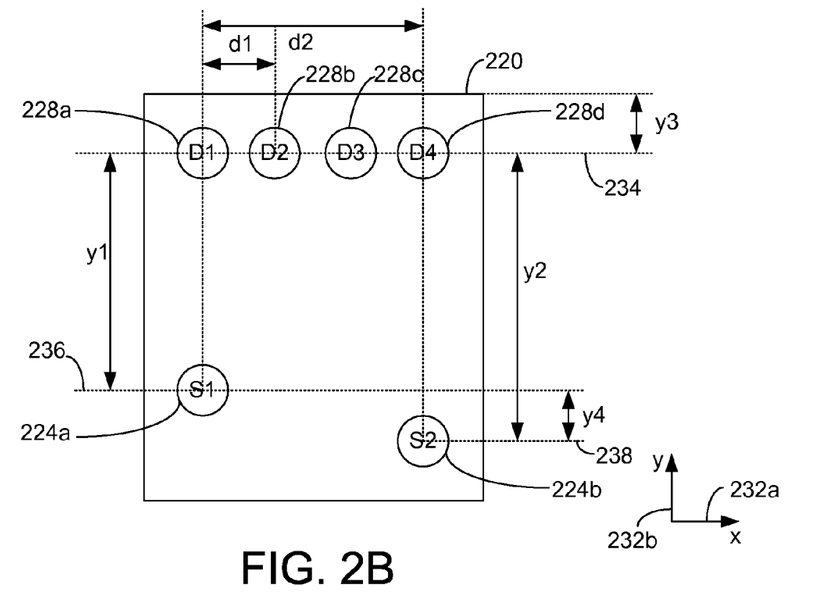
FIG. 2B shows a sensor head with a pair of light sources that are in an offset arrangement relative to a set of four detectors in accordance with a first embodiment of the present invention.

In general, more than two detectors may be used in conjunction with a pair of detectors to monitor oxygen saturation in tissue. By way of example, three or four detectors may be used to detect light that is provided by a pair of sources and is reflected off of a tissue surface. It should be appreciated that some of the light may be reflected from tissue at various depths beneath the tissue surface. That is, light may be reflected off the tissue surface and off of tissue that underlies the surface. The tissue that underlies the surface and allows light to be reflected may be as deep as approximately one centimeter below the surface of the tissue. FIG. 2B shows a sensor head which is arranged to include a pair of sources or, more specifically, source arrangements and four detectors or, more specifically, detector arrangements, in accordance with an embodiment of the present invention. A sensor head 220 includes four detectors 228a-d which are arranged such that centerpoints of detectors 228a-d are substantially aligned along a centerline 234 that is substantially parallel to an x-axis 232a. Sensor head 220 also includes sources 224a, 224b which each include a centerpoint. A centerline 236 that is parallel to x-axis 232a passes through the centerpoint of source 224a, and a centerline 238 that is parallel to x-axis 232a passes through the centerpoint of source 224b.

In the described embodiment, a distance y1 along a y-axis 232b between centerline 234 and centerline 236 is not equal to a distance y2 along y-axis 232b between centerline 234 and centerline 238. Distance y1 may be approximately 0.2 millimeters, as for example approximately 0.197 millimeters, while distance y2 may be approximately 0.24 millimeters, as for example 0.236 millimeters. It should be appreciated that distance y1 and distance y2 may vary widely depending upon any number of factors. The factors include, but are not limited to, the overall size of sources 224a, 224b and detectors 228a-d, the overall size of sensor head 220, and the application for which sensor head 220 is intended. While distance y2 is shown as being greater than distance y1, distance y1 may instead be greater than distance y2. In general, the difference between distance y2 and distance y1 is at least approximately 0.3 millimeters. For example, distance y2 and distance y1 may differ by approximately 1.0 millimeter.

The positioning of sources 224a, 224b and detectors 228a-d may vary widely. By way of example, for an embodiment in which sources 224a, 224b and detectors 228a-d are each approximately 1.0 millimeter in diameter, centerpoints of sources 224a, 224b may be separated by a distance d2 that is approximately 0.22 millimeters relative to x-axis 232a and by a distance y4 that is approximately 0.04 millimeters. Detectors 228a-d may be arranged such that centerline 234 is offset from a top edge of sensor head 220 by a distance y3 that is approximately 0.06 millimeters, and such that adjacent detectors 228a-d are separated by a distance d1 that is between approximately 0.06 millimeters to approximately 0.07 millimeters. Sensor head 220 may have a width of approximately 0.34 millimeters along x-axis 232a and a height of approximately 0.49 millimeters along y-axis 232b when detectors 228a-d and sources 224a, 224b are spaced as described above. However, sensor head 220 generally has dimensions that may vary widely, e.g., dimensions which may vary depending upon the application for which sensor head 220 is intended.

Figure 2C:
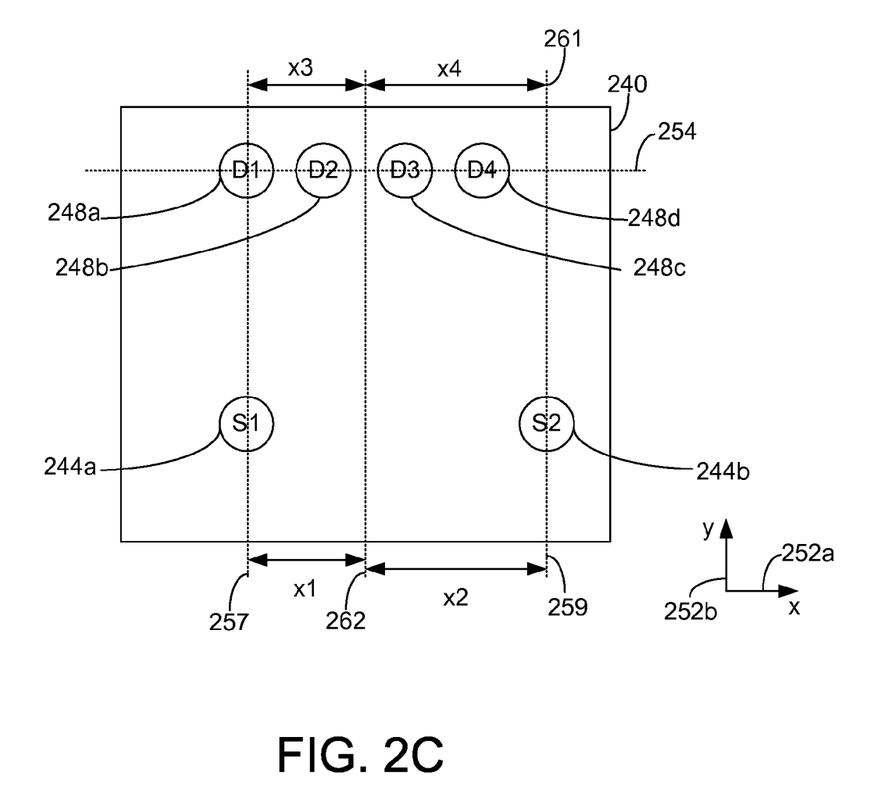
FIG. 2C shows a sensor head with a pair of light sources that are in an offset arrangement relative to a set of four detectors in accordance with a second embodiment of the present invention.

While a lack of symmetry in the positioning of sensors relative to detectors has been described as being such that distances between sensors and detectors are not equal relative to a y-axis, a lack of symmetry may instead or additionally have a lack of symmetry relative to an x-axis. Referring next to FIG. 2C, a sensor head that includes a pair of sources which are in an offset arrangement relative to a set of four detectors with respect to an x-axis will be described. A sensor head 240 includes four detectors 248a-d, although the number of detectors 248a-d may vary. Detectors 248a-d are arranged such that a centerline 254 is substantially parallel to an x-axis 252a and passes through the centerpoint of each detector 248a-d. A first detector 248a and a last detector 248d, i.e., the detectors which are farthest apart relative to x-axis 252a, are used to define a central bisecting line 262 of detectors 248a-d. Central bisecting line 262 is parallel to a y-axis 252b, and is arranged such that a distance x3 from the centerpoint of detector 248a to central bisecting line 262 is substantially equal to a distance x4 from the centerpoint of detector 248d to central bisecting line 262. That is, central bisecting line 262 is arranged to pass through a central midpoint between the centerpoint of detector 248a and the centerpoint of detector 248d such that central bisecting line 262 is substantially perpendicular to centerline 254.

As shown, a centerpoint of a first source 244a and the centerpoint of first detector 248a are aligned along a centerline 257 that is substantially parallel to a y-axis 252b. Similarly, a centerpoint of a second source 244b and the centerpoint of last detector 248d are aligned along a centerline 259 that is substantially parallel to y-axis 252b. It should be appreciated, however, that centerline 257 may not necessarily pass through the centerpoint of first detector 248a, and centerline 259 may not necessarily pass through the centerpoint of last detector 248d. That is, centerline 257 is effectively a line that is substantially parallel to y-axis 252b and passes through first source 244a, while centerline 259 is effectively a line that is substantially parallel to y-axis 252b and passes through second source 244b.

A distance x1 between centerline 257 and central bisecting line 262 is not equal to a distance x2 between centerline 259 and central bisecting line 262. In other words, first source 244a and second source 244b are not equidistant from central bisecting line 262. Hence, sources 244a, 244b are positioned in an offset or unbalanced orientation relative to x-axis 252a.

Figure 3:
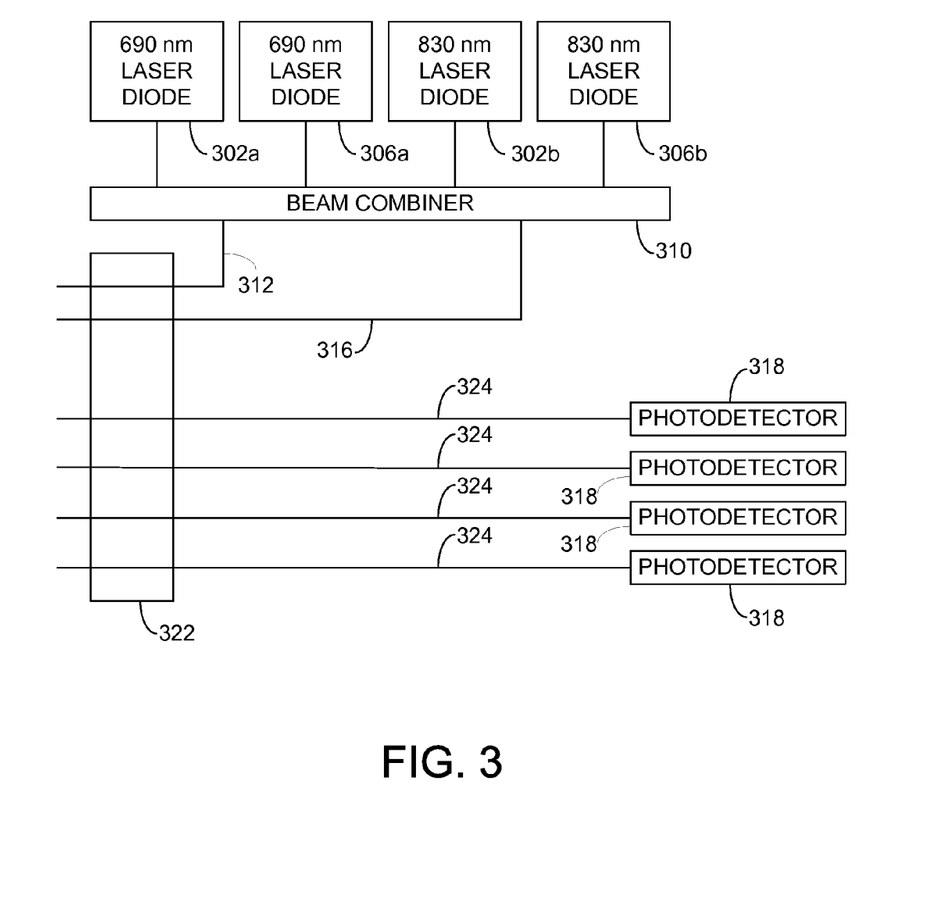
FIG. 3 shows light sources and detectors that are associated with a sensor head in accordance with an embodiment of the present invention.

Sources are typically arranged to emit light of specific wavelengths. As discussed above, light of a lower wavelength emitted by a source may have a wavelength of approximately 690 nanometers, while light of a higher wavelength emitted by the source may have a wavelength of approximately 830 nanometers. FIG. 3 shows light sources and detectors that are associated with a sensor head in accordance with an embodiment of the present invention. A first source may include a laser diode 302a that produces light at a wavelength of approximately 690 nanometers as well as a laser diode 302b that produces light at a wavelength of approximately 830 nanometers. Similarly, a second source may include a laser diode 306a that produces light at a wavelength of approximately 690 nanometers as well as a laser diode 306b that produces light at a wavelength of approximately 830 nanometers.

A beam combiner 310 is arranged to enable light emitted by laser diodes 302a, 302b to be merged onto an optical fiber 312 that is provided to a sensor head 322. Beam combiner 310 is also arranged to enable light emitted by laser diodes 306a, 306b to be merged onto an optical fiber 316 that is provided to sensor head 322. Light transmitted by fibers 312, 316 through a tissue or other surface is reflected, and the reflected light is effectively captured on optical fibers 324 which provide the reflected light to photodetectors 318. Photodetectors 318 are arranged to be sensitive to light with wavelengths of approximately 690 nanometers and approximately 830 nanometers, and typically have a relatively high gain.

Figure 4:
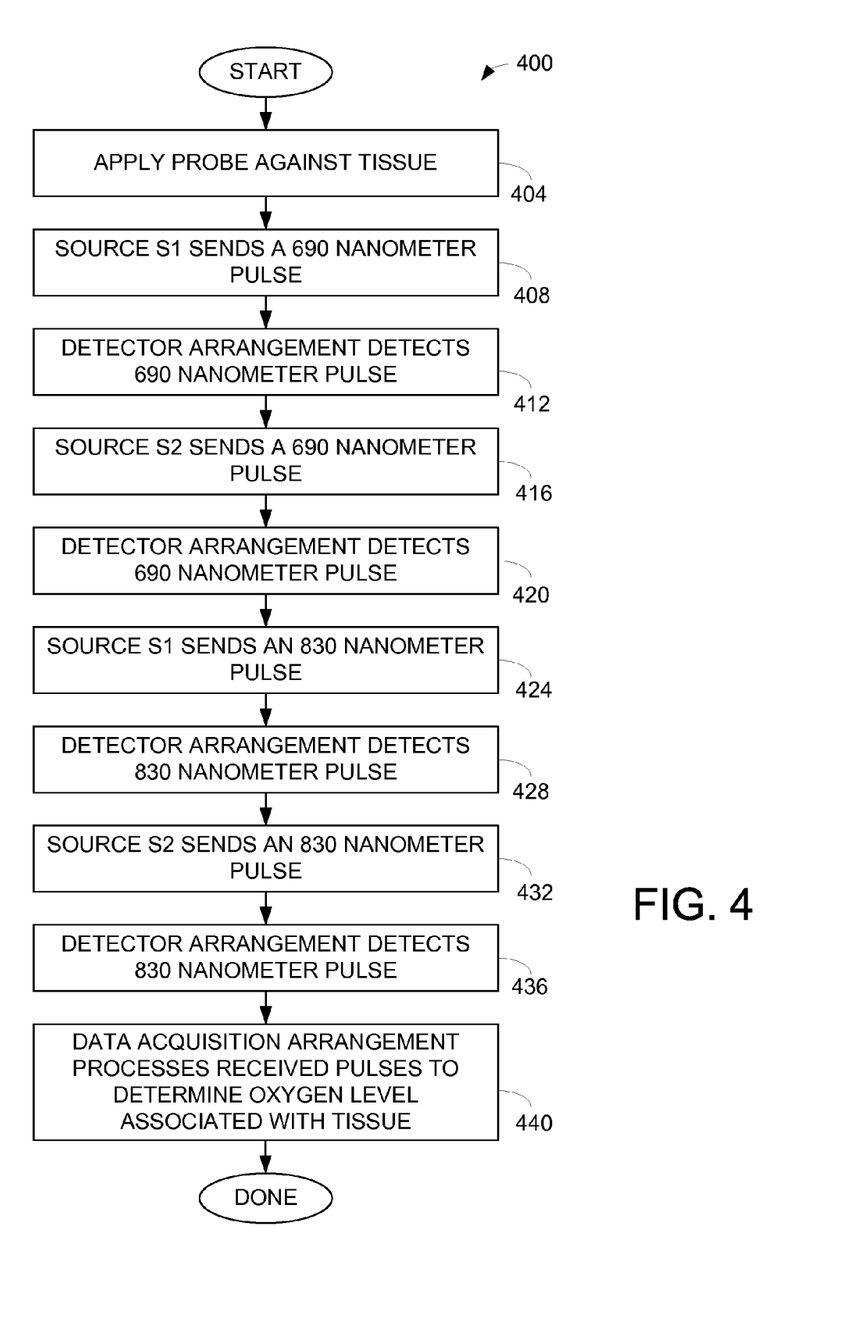
FIG. 4 shows a process flow of utilizing a sensor head with light sources that are in an offset arrangement relative to detectors in accordance with an embodiment of the present invention.

With reference to FIG. 4, one method of monitoring oxygen saturation in tissue using an oximeter with a sensor head in which sources are in an offset orientation relative to detectors will be described in accordance with an embodiment of the present invention. A process 400 of using an oximeter begins at step 404 in which a probe, i.e., a probe that includes a sensor head in which sources are positioned in an offset orientation relative to detectors, is applied against tissue. Once the sensor head is positioned in contact with tissue, a first source S1 associated with the probe sends a lower wavelength pulse of light into the tissue in step 408. The first source S1 may include a laser diode that produces an approximately 690-nanometer wavelength of visible red light, as discussed above, although the lower wavelength of light produced by the first source S1 may vary. In general, first source S1 is a source arrangement that produces light at two wavelengths. Hence, first source S1 may include two substantially separate laser diodes that produce light at two wavelengths.

In step 412, a detector arrangement associated with the probe detects the approximately 690-nanometer light. As discussed above, when the approximately 690-nanometer light is transmitted into the tissue, the approximately 690-nanometer light is reflected into the detector arrangement such that the detectors, e.g., the photodetectors, included in the detector arrangement collect the reflected light. A second source S2 then sends a lower wavelength pulse of light in step 416 which, in the described embodiment, is an approximately 690-nanometer pulse of light. The detector arrangement detects and collects the approximately 690-nanometer reflected light in step 420.

Once the lower wavelength light is transmitted by both the first source S1 and the second source S2, the first source S1 sends a higher wavelength pulse of light into the tissue in step 424. The higher wavelength pulse of light may be an approximately 830-nanometer near-infrared light produced by a laser diode included in first source S1. After the approximately 830-nanometer pulse of light is transmitted into the tissue and reflected, the process flow moves to step 428 in which the detector arrangement detects the reflected light.

The second source S2 sends a higher wavelength pulse of light, e.g., light with an approximately 830-nanometer wavelength, in step 432 that is then reflected off of the tissue and reflected into the detector arrangement in step 436. Once the detector arrangement has received reflected light from both sensors at both the lower wavelength and the higher wavelength, the data acquisition arrangement of the oximeter processes information associated with the received reflected light in step 440. Processing the received reflected light may include executing software or firmware that accounts for or otherwise compensates for attenuation associated with the reflected light in order to determine an oxygen level associated with the tissue. Once the data acquisition arrangement processes the information, the process of monitoring an oxygen saturation level of tissue is completed. It should be understood, however, the steps of FIG. 4 may be repeated to allow for the substantially continuous monitoring of an oxygen saturation level.

Figure 5:
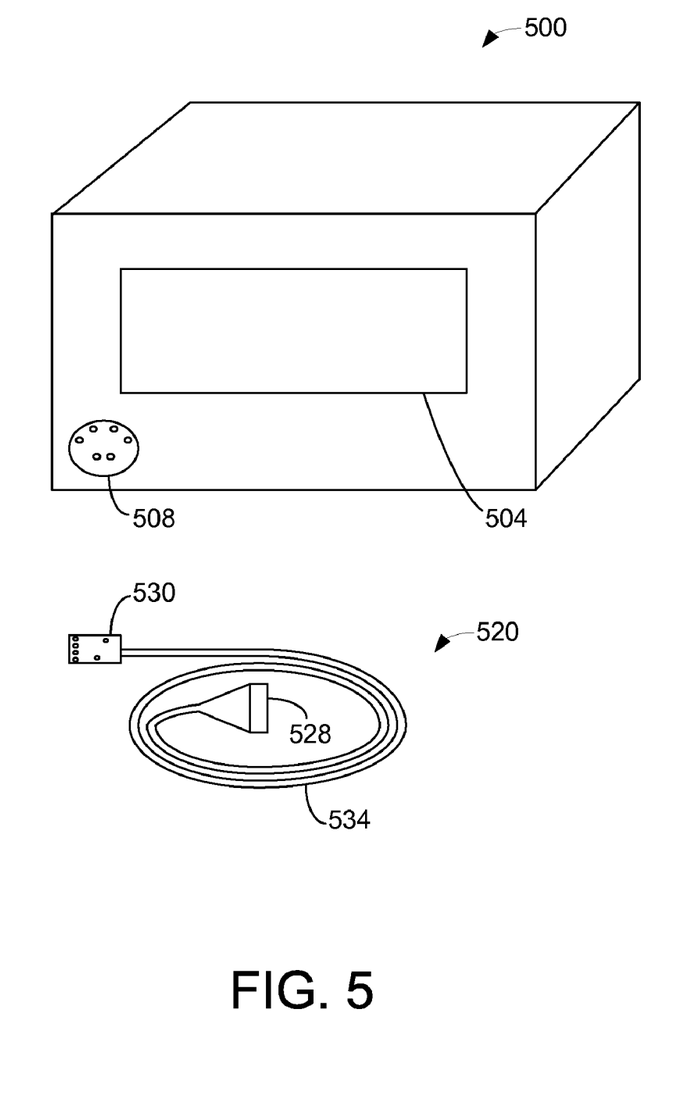
FIG. 5 shows an optical imaging system that includes a console and a decoupleable probe with a sensor head with light sources that are in an offset arrangement relative to detectors in accordance with an embodiment of the present invention.

An oximeter which utilizes a probe with a sensor head of the present invention may include a portable console unit to which the probe may be coupled. As shown in FIG. 5, a console 500 may include a screen 504 that is arranged to display the oxygen saturation level of tissue that is being monitored. Screen 504, which may be a touch screen, may also be arranged to indicate when a probe 520 is in use and to provide warnings to a user that indicate when a monitored oxygen saturation level is potentially problematic.

Console 500 includes a panel connector 508 to which a connector 528 of probe 520 may be connected to allow a sensor head 530 of probe 520 to be used to monitor oxygen saturation levels. Fiber optic cables (not shown) which are used to allow light to pass between connector 528 and sensor head 530 of probe 520 are substantially encased in a cable jacket 534. Console 500 and probe 520 may be a part of the ODISsey™ Tissue Oximeter available commercially from ViOptix, Inc. of Fremont, Calif. ODISsey is a trademark of ViOptix.

Although only a few embodiments of the present invention have been described, it should be understood that the present invention may be embodied in many other specific forms without departing from the spirit or the scope of the present invention. By way of example, the wavelengths emitted by light sources have been described as being approximately 690 nanometers and approximately 830 nanometers. However, substantially any wavelengths may be emitted by the light sources.

The probe on which a sensor head is mounted may have a variety of different configurations. For example, the probe may include a hand piece which facilitates spot measurements of tissue. Additionally, the configuration of a sensor head may also vary depending upon the particular application for which the sensor head is to be used.

A probe, e.g., a fiber optic probe, on which a sensor head is mounted uses fiber optic cable to carry an optical signal to and from tissue. The fiber optic cable may be of any length, and may contain one dual wavelength source fiber for each source and one detector fiber for each detector. In one embodiment, the fiber optic cable may be approximately three meters long, and the source and detector fibers may each have diameters of approximately one millimeter.

A centerpoint of a source optical fiber and a centerpoint of a detector optical fiber have generally been described as being centerpoints of fibers that are substantially circular in orientation. It should be appreciated that in some instances, when a fiber is not substantially circular in orientation, the centerpoint may be an approximate centerpoint of the fiber.

The steps associated with the various methods of the present invention may be widely varied. Steps may be added, altered, removed, and reordered without departing from the spirit or the scope of the present invention. Therefore, the present examples are to be considered as illustrative and not restrictive, and the invention is not to be limited to the details given in this application, but may be modified within the scope of the appended claims.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A device comprising:
   a first source structure;
   a first detector structure;
   a second detector structure; and
   a third detector structure, wherein the second detector structure is between the first and third detector structures,
   the first source structure, first detector structure, and third detector structure form vertices of a first right triangle, and a first hypotenuse of the first right triangle extends from the first source structure to the third detector structure without touching another source or detector structure.

2. The device of claim 1 comprising:
   a second source structure, wherein the second source structure, first detector structure, and third detector structure form vertices of a second right triangle, and a second hypotenuse of the second right triangle extends from the second source structure to the first detector structure without touching another source or detector structure.

3. The device of claim 2 wherein a length of the first hypotenuse is different from a length of the second hypotenuse.

4. The device of claim 1 wherein the first, second, and third detector structures are arranged in a line.

5. The device of claim 1 comprising a fourth detector structure between the first and third detector structures.

6. The device of claim 1 wherein the first source structure and first detector structure comprise optical fiber.

7. The device of claim 1 wherein the first source structure and first detector structure comprise the same cross-sectional shape.

8. The device of claim 1 wherein the first source structure and first detector structure comprise the same cross-sectional area.

9. A medical device that measures oxygen saturation of a tissue comprising the device of claim 1.

10. A device comprising:
    a first source structure;
    a first detector structure;
    a second detector structure; and
    a third detector structure, wherein the second detector structure is between the first and third detector structures,
    the first source structure, first detector structure, and third detector structure form vertices of a first triangle having an obtuse angle, and a first longest side of the first triangle extends from the first source structure to the third detector structure without touching another source or detector structure.

11. The device of claim 10 comprising:
    a second source structure, wherein the second source structure, first detector structure, and third detector structure form vertices of a second triangle, and a second longest side of the second triangle extends from the second source structure to the first detector structure without touching another source or detector structure.

12. The device of claim 11 wherein a length of the first longest side is different from a length of the second longest side.

13. The device of claim 11 wherein the second triangle has an obtuse angle.

14. The device of claim 11 wherein the second triangle has a right angle.

15. The device of claim 10 wherein the first, second, and third detector structures are arranged in a line.

16. The device of claim 10 further comprising a fourth detector structure between the first and third detector structures.

17. The device of claim 10 wherein the first source structure and first detector structure comprise optical fiber.

18. The device of claim 10 wherein the first source structure and first detector structure comprise the same cross-sectional shape.

19. The device of claim 10 wherein the first source structure and first detector structure comprise the same cross-sectional area.

20. A medical device that measures oxygen saturation of a tissue comprising the device of claim 10.

21. A device comprising:
    a first source structure;
    a second source structure;
    a first detector structure, wherein the first detector structure comprises optical fiber; and
    a second detector structure, wherein a first distance extends between the first source structure and the first detector structure without touching another source or detector structure,
    a second distance extends between the second source structure and the second detector structure without touching another source or detector structure, and
    the first distance is different from the second distance.

22. The device of claim 21 wherein the first distance is greater than the second distance.

23. The device of claim 21 wherein the first distance is greater than the second distance by at least 0.3 millimeters.

24. The device of claim 21 wherein the first source structure comprises optical fiber.

25. The device of claim 21 wherein the first source structure and first detector structure comprise the same cross-sectional shape.

26. The device of claim 21 wherein the first source structure and first detector structure comprise the same cross-sectional area.

27. The device of claim 21 wherein a third distance is between the second source structure and the first detector structure, a fourth distance is between the first source structure and the second detector structure, the first distance is different from the second, third, and fourth distances, the second distance is different from the third and fourth distances, and the third distance is different from the fourth distance.

28. A medical device that measures oxygen saturation of a tissue comprising a probe of claim 21.

* * * * *